(12) United States Patent
Panting (10) Patent No.: US 8,825,174 B2
(45) Date of Patent: Sep. 2, 2014

(54) THERAPEUTIC ELECTRIC ANTIOXIDANT CLOTHING APPARATUS AND METHOD

(75) Inventor: Jacqueline Panting, College Park, MD (US)

(73) Assignee: Integrity Research Institute, Beltsville, MD (US)

( * ) Notice: Subject to any disclaimer, the term of this patent is extended or adjusted under 35 U.S.C. 154(b) by 96 days.

(21) Appl. No.: 13/135,140

(22) Filed: Jun. 27, 2011

(65) Prior Publication Data

US 2012/0016446 A1 Jan. 19, 2012

Related U.S. Application Data

(60) Provisional application No. 61/358,916, filed on Jun. 27, 2010.

(51) Int. Cl.
| | |
|---|---|
| *A61N 1/00* | (2006.01) |
| *A61B 5/04* | (2006.01) |
| *A61N 1/20* | (2006.01) |
| *A61N 1/04* | (2006.01) |
| *A61N 1/32* | (2006.01) |

(52) U.S. Cl.
CPC .............. *A61N 1/205* (2013.01); *A61N 1/0484* (2013.01); *A61N 1/32* (2013.01)
USPC .................. 607/62; 607/2; 600/386; 600/388

(58) Field of Classification Search
USPC ................................ 607/2, 62; 600/386, 388
See application file for complete search history.

(56) References Cited

U.S. PATENT DOCUMENTS

| | | | |
|---|---|---|---|
| 3,014,818 | A | 12/1961 | Campbell |
| 3,971,366 | A | 7/1976 | Motoyama |
| 4,364,739 | A | 12/1982 | Tomibe |
| 4,410,593 | A | 10/1983 | Tomibe |
| 4,993,413 | A | 2/1991 | McLeod |
| 4,996,987 | A | 3/1991 | Petrofsky |
| 5,607,461 | A | 3/1997 | Lathrop |
| 6,011,398 | A | 1/2000 | Bald |
| 6,217,604 | B1 | 4/2001 | Azure |
| 6,472,888 | B2 | 10/2002 | Oguma |
| 6,751,506 | B2 | 6/2004 | Shealy |
| 2004/0087228 | A1 * | 5/2004 | Van Heerden et al. ........... 442/4 |

* cited by examiner

Primary Examiner — Nicole F Lavert (57) ABSTRACT

A process for introducing therapeutic doses of electric antioxidants to the human skin with conductive portions in clothing for electrically contacting the skin, for applying direct current, pulsed direct current, or alternating current electricity of various voltage and current levels, for conductive wiring fiber interwoven in clothing, and for electronically controlling the doses of electric antioxidants in microcurrent doses applied percutaneously or transcutaneously to the human skin. A preferred embodiment includes the process for applying clothing that is skin tight, with or without a control module imbedded in the clothing or optionally, a wireless and remote control module for administering the therapeutic doses of electric antioxidants to the skin of the head, feet, legs, hips, or upper torso.

13 Claims, 9 Drawing Sheets

Prior Art

THERAPEUTIC ELECTRIC ANTIOXIDANT CLOTHING APPARATUS AND METHOD

This nonprovisional patent application claims priority benefits from the provisional application No. 61/358,916 filed Jun. 27, 2010 and from the Certification and Request for Extended Missing Parts Pilot Program, sole inventor Jacqueline Panting.

TECHNICAL FIELD

The present invention relates to the field of electrotherapy, bioelectricity, bioelectromagnetics, medical electricity and electromedicine. Particularly, the invention involves the novel implementation of self-powered electric therapeutic clothing with the novel addition of imbedded wiring in order to provide antioxidant microcurrent electricity delivered to the human skin at strategic acupuncture points using an integrated constant voltage, constant current, variable voltage or variable current circuit. The present invention further comprises transcutaneous and percutaneous applications for electron delivery in microdoses for health.

BACKGROUND OF THE INVENTION

Historically, as far back as 1890, the American Electro-Therapeutic Association conducted annual conferences on the therapeutic use of electricity and electrical devices by physicians on ailing patients. Some involved current flow through the patient with direct contact to electricity producing machines, while others were electrically powered devices presenting strong electric fields in the vicinity of the patient. The great electrical engineer, Nikola Tesla states that "One of the early observed and remarkable features of the high frequency currents, and one which was chiefly of interest to the physician, was their apparent harmlessness which made it possible to pass relatively great amounts of electrical energy through the body of a person without causing pain or serious discomfort" (Tesla, Nikola. "High Frequency Oscillators for Electro-Therapeutic and Other Purposes," *The Electrical Engineer*, Vol. XXVI, No. 550, Nov. 17, 1898, p. 477). At first, only direct current (DC) devices were utilized in the medical doctor's office for relieving pain and vibrating female patients who were routinely diagnosed with "hysteria." Tesla also correctly concluded that bodily "tissues are condensers" (capacitors) in his 1898 paper. Today, the average capacitance of bodily tissue is well known and confirmed to be about 100-300 pF (Sheppard, A. R., et al., *Biological Effects of Electric and Magnetic Fields of Extremely Low Frequency*, New York University Press, New York, 1977, Ch. 5, p. 4-18).

A pioneering medical doctor in the 1960's, Robert O. Becker, M.D., is most famous for his book, *The Body Electric, Electromagnetism and the Foundation of Life*, (William Morrow & Co., New York, 1985) which gives an autobiographical account of his life's experiences with bioelectromagnetics, the science of using electromagnetic fields for biological benefits and effects. As documented in his book, Dr. Becker was instrumental in establishing that the Chinese meridians of the body which connect traditional acupuncture points are skin pathways of decreased electrical resistance. This bioelectric principle has not been utilized in any medical or electrotherapeutic device to date. Dr. Becker also discovered a host of other bioelectric effects within the body as well, such as electrostimulating limb-regeneration in mammals.

While prior art transcutaneous electrical nerve stimulators (TENS) are typically utilized to mask pain in the body before they reach the brain, giving the subject an apparent relief of the pain, they typically work only with a battery-operated electronic box connected by wires to the subject. Furthermore, such electric nerve stimulators operate in the hundreds of milliampere (mA) range rather than in the microampere (uA) range of the present invention. While electric nerve stimulators are usually applied only over a short period of time, the present invention can be used for any length of time, even up to twenty-four hours a day for health and longevity improvement. A good reference book on this therapeutic field is *Electrotherapy Explained: Principles and Practice* by Val Robertson. FDA-approved TENS units relieve pain and provide up to a few hundred milliampere current levels for nerve stimulation only, such as U.S. Pat. No. 4,803,986 that attempts to be ergonomic in its design.

Another area of concern affecting the health and well-being of a large number of the population is chronic fatigue syndrome (CFS). The causes for CFS are still undetermined. Some studies suggest multiple nutrient deficiencies can trigger chronic fatigue. Therefore, proper nutrition, consisting of a well balanced diet is vitally important. Fresh fruits and raw foods are especially recommended. Herbs that are helpful include ginkgo, astragalus, red clover, dandelion and short term use of echinacea to help boost the immune system, which is always affected by CFS, as is commonly taught in naturopathy. To help improve the interrupted sleep pattern, valerian root or melatonin at bedtime is also helpful.

Although numerous studies have been conducted to find the underlying causes of CFS, none have succeeded in understanding its physiological or chemical pathways. Some studies have shown that deficiencies of the adrenal or thyroid glands have been found in CFS patients. This has prompted the medical opinion that stress can trigger CFS, whether it is of mental or physical origin. Therefore energy boosting therapies as well as vitamins and antioxidant supplementation which are known to combat free radical proliferation is now considered to be extremely important.

The process by which free radicals deplete cellular energy is well known. Free radical proliferation is linked to pathological changes that cause cellular malfunction or mutation (i.e., cancer) as well as protein and collagen degradation, most noticeable in visible facial skin wrinkling. Free radicals also play a large role in causing damage to all cells of the body but particularly the immune system. Free radicals also deplete cellular energy by interfering with mitochondrial function and contribute to shortened lifespan, according to studies with animal species and are the main cause of aging. Cellular energy generation in the mitochondria is both a key source and key target of oxidative stress in the cells. Seeking an electron to complete the radical which is an ion that is missing an electron, free radicals cause chain reactions as electrons are ripped from molecules, creating another free radical. Standard college organic chemistry textbooks (e.g., Streitwieser, *Introduction to Organic Chemistry*, $2^{nd}$ ed., MacMillan, 1981, p. 101) emphasize that since the chlorine molecule ($Cl_2$) dissociates at body temperature, a warm shower is enough to create a chlorine radical ($Cl^-$) bath as a person takes a shower in the morning. The Streitwieser textbook also details the number of free radical chain reaction (multiplications) that every one of the chlorine radicals creates, which is an astonishing 10,000 additional free radicals. Free radicals are all-pervading and a leading cause of the aging process because they are able to multiply so readily while doing irreparable damage if antioxidants are absent. The only antidote presently available for such an onslaught of daily shower skin aging agents is an activated charcoal shower filter, which is relatively unknown to the general public. However, with free radicals in the air, water and food, only an internal source of antioxidants can feasibly attack the majority of the free radicals in the biological terrain consisting of organs, tissue, blood stream and lymphatic system. The present invention counteracts this major cause of aging by a novel and unobvious technological innovation in healing and electrotherapy.

Cellular energy generation in the mitochondria is another area of concern since it is both a key source and key target of oxidative stress in the cell. One can therefore envision a model whereby the inevitable increased production of free radicals due to energy generation as well as stress and disease compromises mitochondrial efficiency and also energy output in a detrimental feedback loop. Therefore, in the short term, sports professionals will have a decrease in performance after an hour or two of competition and in the long term, most aging humans experience a decrease of vitality and energy as they move into their senior years.

Antioxidants such as vitamin A, vitamin E, vitamin C, selenium and coenzyme Q10 supply free electrons and are usually prescribed by naturopathic doctors in order to provide limited relief in counteracting free radical ravages, as long as they are taken regularly. However, vitamin C is water soluble and is excreted from the body in about three hours so ideally one should supplement with vitamin C every three hours to be able to handle stress, which is known to deplete the body of vitamin C. Furthermore, humans as opposed to animals do not make vitamin C in their bodies automatically in response to stress.

The innovative discovery by this inventor is that electronic antioxidants can be produced by bioelectromagnetics (BEM) therapy on a continuous or programmed basis through electric therapeutic clothing. While there are external devices that produce the same electrons provided by antioxidant pills and also satisfy and terminate free radicals even more effectively because of their greater concentration of antioxidant quantity and continuous release modality, none have been incorporated into electrified clothing with strategic conductive pads at specifically chosen acupuncture points, designed by a naturopathic doctor such as this inventor. Electricity itself, even in microcurrent doses, abundantly supplies the key ingredient usually found only in encapsulated antioxidant supplements . . . the electron. The discovery that the electron itself is the main active ingredient in antioxidants has been documented in books such as, *Energy Medicine* by Dr. James Oschman and *Bioelectromagnetic Healing* by Thomas Valone, PhD. However, the concept of being conveniently and therapeutically designed to contact the skin at strategic points for hours through an electrified wearable clothing product has not been manufactured or sold to the public.

An example of the use of the invention title in a different sense is Japanese patent JP 407229004A issued for "electric clothing" by Kazumi is controllable by a liquid crystal display and has fine wires throughout the fabric in a network shape. However, the clothing is plugged into a receptacle and external power source with a cable attached to the clothing, only for the purpose of displaying an image, like a video display terminal, directly on the clothing. The Kazumi invention has no therapeutic benefits whatsoever.

Other areas of electricity being applied to the human body includes U.S. Pat. No. 6,472,888 which is drawn to a device for measuring bioelectric impedance which is not used or designed for therapeutic purposes.

An example of a bioelectromagnetic handheld device that is a therapy instrument is a microelectroneural stimulation (MENS) unit with a battery-powered low voltage current device, usually between 1 μA and 1000 μA. One microamp (μA) is $1/1000$ of a milliamp (mA), so 1000 μA equals 1 mA. Most TENS devices have a working range of 2-250 mA. However, no MENS therapy device has been modified to work with conductive fibers in a clothing product.

An example of an electrically conducting fiber suitable for use with this invention is U.S. Pat. No. 4,410,593 which teaches a method of manufacture that allows the fibers to absorb monovalent copper ions and convert them to copper sulfide and still retain the characteristics of acrylic fiber.

Another example is U.S. Pat. No. 3,014,818 which teaches the process of converting metal salts to free metal particles that adhere to the surface of the clothing fibers forming a plated coating. However, it will not survive too many repeated clothes washing cycles.

U.S. Pat. No. 4,364,739 describes and claims a method for making electrically conducting fiber which comprises subjecting acrylic and modacrylic fibers to a first heat treatment in a bath containing a copper compound and a reducing agent to absorb monovalent copper ions within the fiber and then subjecting the fiber to a second heat treatment in the presence of a sulfur compound to form copper sulfide. This method has the advantage that a considerable increase in electrical conductivity results from the treatment and the fibers formed can be washed repeatedly without a substantial reduction in the electrical conductivity.

There are also many patents devoted to delivering electrical stimulus to human tissue with an exogenous device and movable, free electrodes such as U.S. Pat. No. 5,607,461 or the power muscle stimulator U.S. Pat. No. 4,996,987. However, none of them operate in the microcurrent range and have been integrated into clothing to counteract free radicals.

An example of an electrotherapy invention is the U.S. Pat. No. 6,217,604 awarded to Larry Azure and Jim Girard that describes a high voltage Tesla coil electron producing device attached to noble gas tubes to treat HIV/AIDS, according to the disclosure that cites a study done with his device, with only short term exposure at a short distance of a few feet from the patients. The electrotherapy device was used in an HIV+ ten-patient clinical study in 1996 by the New York Health and Healing Center that relieved pain and the majority (50% to 84%) of symptoms in nine out of the ten patients. Such a product is expensive, large and even a shock hazard however. It also does not have a miniature counterpart that has been integrated into clothing along with its power source for microcurrent applications.

Another example is the "Electrical Stimulation to Reduce Free Radical Levels" U.S. Pat. No. 6,751,506 by Norman Shealy, MD, which is hereby incorporated in its entirety by reference. The Shealy patent describes the vast theory and practice related to free radical damage and the electrical stimulation approach to solving it using exogenous electrodes temporarily applied to the skin to deliver pulsating high frequency doses of AC electricity. The Shealy patent also proves the case for electronic antioxidants being superior to capsules and pills used for oral supplementation. However, the ShealyTENS unit is inconvenient to use on a daily basis and requires repeated hand placement of electrodes without adhesive in various locations on the body. The Shealy patent does not include a microcurrent application imbedded in clothing for ease of use.

SUMMARY OF THE INVENTION

The present invention relates generally to a percutaneous and transcutaneous process of applying electric antioxidants to the human body through advantageously designed wearable clothing with electrically conductive sections and a self-contained, renewable energy power source, in the nanoampere (nA), microampere (μA), up to two milliamperes (2 mA) in current.

It is based in part on research related to accelerated wound healing, which is a vital necessity for sports competitors and medical professionals. Presentations at the 8th International Congress of the American Academy of Anti-Aging Medicine in Las Vegas, indicated that microcurrent electrotherapy can provide painless relief for the estimated 2 percent of Americans living with wounds that don't heal. "We don't completely understand why it works," said Dr. Alfred J. Koonin, referring to a clinical study of an electrical wound healing instrument device. "What we do understand is that the device seems to act as an ultra-powerful antioxidant that knocks out infection, stimulates blood flow and encourages cell regeneration. Here Dr. Koonin corroborates the scientific validity of electrotherapeutic microcurrent and its connection to providing electronic antioxidants directly to the human cellular stratum. The present invention dramatically improves upon any such tabletop wound healing device and every one of the TENS devices on the market by integrating, miniaturizing and interweaving the electrical wiring and required self-powering circuitry into wearable clothing which is portable.

The electric therapeutic clothing invention discloses a comfortable, stretchable, skin-tight electric shirt, separate electric tights, and even electric gloves, headbands, skullcaps, goggles with band, armbands, legbands, underwear, socks or shoes, each of which have electrotherapeutic circuits that provide a range of between nanoamperes to microamperes of electrical current continuously to the body at specific acupuncture points which are known to be areas of low resistance. An alternate embodiment can be a complete body stocking or body suit with similar design. This preferred current level of the present invention is called a "trickle current. A small flexible, heat to electricity converter, vibration energy harvester made from piezoelectric material, or small, thin, flexible, plastic photovoltaic solar panels that also convert energy from infrared radiation, such as those from Konarka, also make the invention self-contained and eliminate the need for a traditional battery or an external power source.

The present invention utilizing microcurrent in skin tight clothing and clothing accessories, because of its close proximity to the body's endogenous current, is thought to work on a more cellular level. It has been theorized that healthy tissue is the result of the direct flow of electrical current throughout the body along acupuncture meridians, as explained in *The Body Electric* by Robert Becker, M.D. previously mentioned. Electrical balance is disrupted when the body is injured at a particular site, causing the electrical current to change course. The use of microcurrent over the injured site will help the body to realign this flow, thus aid in tissue repair. It's been found that ATP (adenosine triphosphate) in the cell helps to promote protein synthesis and healing, as well as provides the basic energy the cell needs for metabolism. The lack of ATP due to trauma of the tissue results in the decreased production of sodium and an increase in metabolic wastes and free radicals, which causes localized pain. The use of microcurrent at an injured area in the range of 100-600 μA not only helps to realign the body's electrical current, improve vascular permeability and increase the production of ATP but also results in approximately 50% reduction in the normal healing time and recovery, as well as relieving the pain by quenching the free radicals that cause the pain (Cheng. Et al., "The effects of electric current on ATP generation, protein synthesis and membrane transport in rat skin", *Clinical Orthopedics and Related Research*, November-December, 1982; 171).

Another embodiment of the present invention is with specially designed therapeutic electric clothing headbands, elastic band or stretchable skullcap for the head, applying a completely wearable and portable clothing incorporation of transcranial direct current stimulation (tDCS), which is a safe, non-invasive technique that temporarily increases or decreases excitability of populations of neurons. In particular, tDCS can be used to manipulate the competition between the left and right hemisphere by inhibiting and/or disinhibiting certain networks in the brain. Recently, short treatments of tDCS, up to 2 mA, have been found to facilitate insight and memory recall, "enabling access to a level of perception normally hidden from conscious awareness." Reference: Richard P. Chi, Allan W. Snyder. Facilitate Insight by Non-Invasive Brain Stimulation. PLoS ONE, 2011; 6 (2): e16655 DOI: 10.1371/journal.pone.0016655

Although the invention is illustrated and described herein as embodied, it is nevertheless not intended to be limited to the details shown, since various modifications and structural changes may be made therein without departing from the spirit of the invention and within the scope and range of equivalents.

The construction and method of operation of the invention, however, together with the additional objects and advantages thereof will be best understood from the following description of specific embodiments when read in connection with the accompanying drawings.

DETAILED DESCRIPTION

Theory of Operation

Science has long been aware of an electrical phenomenon called the "current of injury". This happens when tissue in the body undergoes trauma or microscopic damage to an area of skin. When skin cells are pierced, as with an acupuncture needle, they start leaking positively charged ions, which are equivalent to free radicals, into the surrounding areas of tissue and weak electrical battery-like charge is created. This electric current is called the current of injury, which is known to stimulate a healing response from the nearby cells. This does not explain how stimulating acupoints with low level, non-invasive lasers could achieve the same therapeutic effects (see *Vibrational Medicine for the 21 Century*, Richard Gerber M.D., Eagle Brook, N.Y., 2000). The electrical conductivity of acupoints has been known for several decades thanks to the work of Nakatani in the 1950s and by Dr. Robert Becker in the 1970s. Becker's work on the Large Intestine and the Pericardium meridians found that the points along these channels showed significantly more electrical conductivity than areas of skin with non-acupoints. In 1986 German scientist Fritz-Albert Popp and Chinese biologist, Chang-Lin Zhang developed a model they called the "Standing Wave Superposition Hypothesis". This research attempts to accommodate the holographic nature of acupuncture such as the homunculus or miniature representation of the whole body represented in the ears and the feet. The theory also strives to explain the anomalous skin resistance properties of acupuncture points as well as the apparent interconnectivity between them. In the Zhang-Popp model, it is shown that the body is composed of sodium, potassium and other electrically charged inorganic ions such as proteins and DNA which when accelerated will emit EM radiation in accordance with conventional physical theory. With these many types of charges oscillating in the body, an interference pattern is produced formed by the various waves of various wavelengths. The highest combination of wave amplitudes forms the acupuncture points and meridians by means of constructive interference. At these points the skin is at the highest in electrical conductivity. This conductivity depends on the internal electrical field, which is determined by the interference pattern from the superposition of the numerous waves ("Can Western Science Provide a Foundation for Acupuncture"—Beverly Rubik, PhD. *Alternative Therapies*, September 1995, Vol. 1 Number 4). Hence, the standing wave pattern of a sick person would have a varied pattern from that of a healthier person. The treatment of acupuncture with needles in the acupoints would cause a disturbance in the standard wave pattern caused by new boundaries formed by the needle. The needle activates the current of injury response resulting in a change in the EM field, producing changes in the biological response, which may promote healing. It is this theory, which implicates the EM fields of the entire body.

The principle of the Connective Tissue Continuum is another approach at viewing the correlation of acupuncture to the bioelectromagnetic theory. From a cellular level through to the body's connective tissue, these living organisms are considered a continuum. Not only is the entire cell now known to be mechanically and electrically interconnected in a "solid state", but, all the cells in the body are in turn interconnected to one another via the connective tissues. (see Clegg J. S. and Drost-Hansen W, "On the biochemistry and cell physiology of water." In: Hochachka and Mommsen (eds.), *Biochemistry and Molecular Biology of Fishes*, Elsevier Science, vol.1, ch.1, pp.1-23, 1991 and Oschman, James L. (October 1996-January 1998) "What is 'Healing Energy'? The Scientific Basis of Energy Medicine", *Journal of Bodywork and Movement Therapies*, Part 1-6, Kreisand Boesch, 1994).

The function of connective tissues is to keep the body organized, acting as a lace work between the major organs and tissues, to strengthen the wall of arteries, veins, intestines and pathways and to provide fascia and the skeletal structure attachment to the muscles. It is believed that connective tissues may be largely responsible for the rapid intercommunication that enables our body to function effectively as a coherent whole, and is therefore central to our health and well-being. Recent studies with nuclear magnetic resonance has shown that the muscles in living human subjects provide evidence of a "liquid-crystalline-like" structure. Liquid crystals usually undergo rapid changes in phases or transitions when exposed to electromagnetic fields. Liquid crystals will also respond to changes in temperature, hydration, pressure and shear forces. Biological liquid crystals carry static electric charges and are therefore electrically conductive. They are also influenced by pH, salt concentration and dielectric constant of the solvent as well as electric antioxidants or free electrons.

Another reference is *Microcurrent Electro-Acupuncture* by Starwyn (Desert Heart Press, Phoenix, 2002), a textbook that provides a resource to microcurrent applications. As an example, microcurrent therapy has also been studied as a treatment for macular degeneration and shown for 16 out of 18 patients to slow down the progression of the disease and "actually promote healing". Those with retinitis pigmentosa also showed improvement in 62 out of 78 patients (Starwyn, D., "Is Microcurrent Therapy Effective for Treatment of Macular Degeneration?", *Acupuncture Today*, Vol. 7, Issue 5, May, 2006).

According to a study conducted at Stanford University and published in the *Proceedings of the National Academy of Sciences*, with 58 women ranging from 20 to 50, where blood was drawn periodically and all of the women interviewed, the most stressed women in the study had cells that looked ten years older than their chronological age. The stressed women also had higher levels of free radicals reported to be "highly reactive molecules that can damage DNA" (Lemonick, *Time*, "The Ravages of Stress", Dec. 13, 2004, p. 45). Therefore, the presence of free radicals in the body is directly related to aging and its reduction can be an anti-aging benefit.

The efficacy of the present invention is verified with the periodic application and testing methods available to medical professionals for assaying the levels of free radicals in the blood. One product that does not involve drawing blood is the medical testing device, PharmanexMD which offers a Raman scattering method of assessing the caratenoid levels in the blood through the skin. Application of the present invention will invariably show an increase in caratenoid levels after a period of application of electric antioxidants, which certifies the proper operation of this novel clothing product. Testing for the results of the therapeutic electric clothing is preferred to be done with the PharmanexMD. In addition, the Motoyama diagnosing meter for functional condition inspection of the internal organs and autonomic nerves (U.S. Pat. No. 3,971,366) or the Aculife invented by Dr. Lin can be used to test the acupuncture point conditions before and after.

Figure 1:
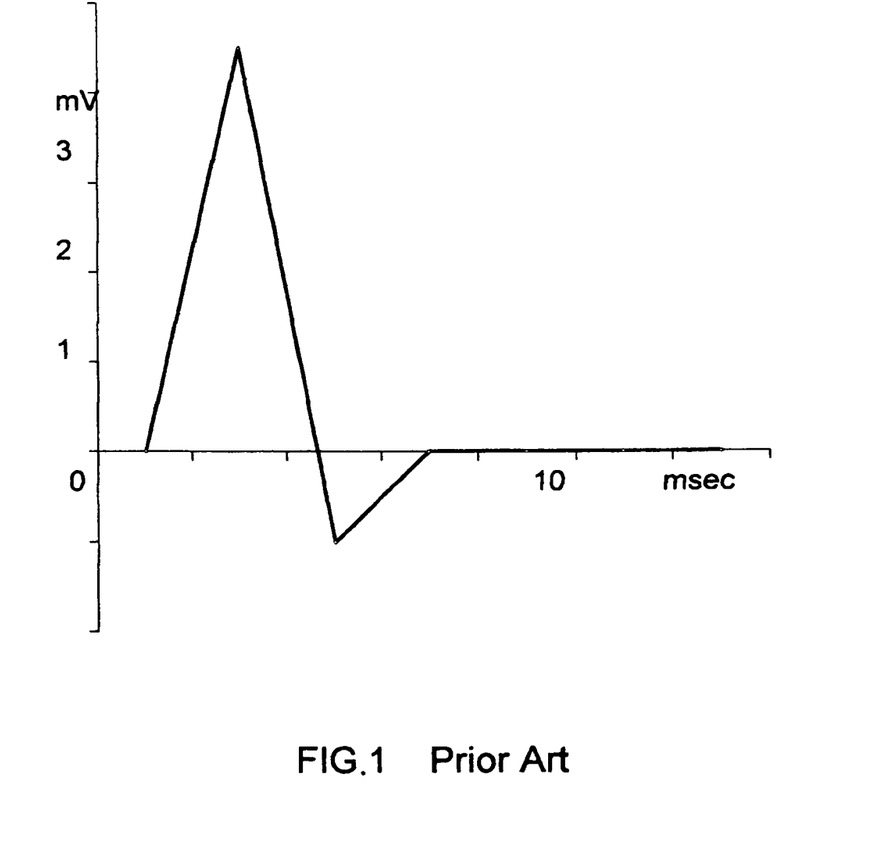
FIG. 1 shows a prior art bone healing electrotherapy pulsed waveform
Figure 2:
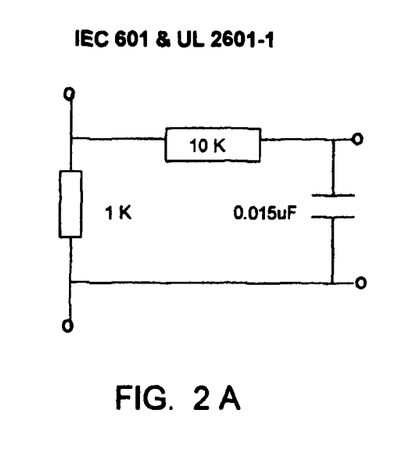
FIG. 2A-2E are examples of various human equivalent circuits.

FIG. 1 shows the pulsed current used in the Prior Art bone healing technology made popular through the efforts of three doctors, Arthur Pilla, PhD, Andrew Bassett, M.D. and Robert Becker, M.D. which uses a pulsed waveform inducing milliamperes of current to transport calcium ions across the cell membranes and speed healing of bone and cartilage in half the time, on the average, such as with the U.S. Pat. No. 4,993,413 where a pulsed magnetic field from a portable generator induces the healing current.

The electrical current used in the present invention is in the range of microamperes ("microcurrent") and is so small that it is rarely felt physically. However, in the biological terrain it is surprisingly robust, with a high quantity of antioxidant electrons and therefore, has a profound effect. As an example, each ampere of current is physically equivalent to 1 coulomb per second of charge transfer. However, each electron is equal to only $1.6 \times 10^{-19}$ coulombs of charge and yet each single electron can stop a single free radical from replicating thousands of times, such as the chlorine ion radical from chlorinated municipal water. With the above-mentioned ampere-coulomb-electron details, we find that one microampere ("microcurrent") of current will equal approximately $10^{13}$ electrons per second (10 trillion electrons per second). Therefore, a microcurrent therapeutic electric clothing product has the potential to quench a maximum of 10 trillion free radicals per second, which explains why this novel therapeutic invention has a macroscopic impact on health and healing.

In FIG. 2A through FIG. 2E, examples of different human equivalent circuits are shown from U.S. Pat. No. 6,011,398. Organizations such as Underwriter's Laboratories (UL), Canadian Standards Association (CSA), Association of German Engineers (VDE), British Standards Institution (BSI), and Japanese Standards Association (WS) and other private and governmental testing agencies have selected a variety of other human equivalent circuits. Any product sold in jurisdictions covered by more than one of these organizations must be tested using multiple human equivalent circuits.

Figure 3:
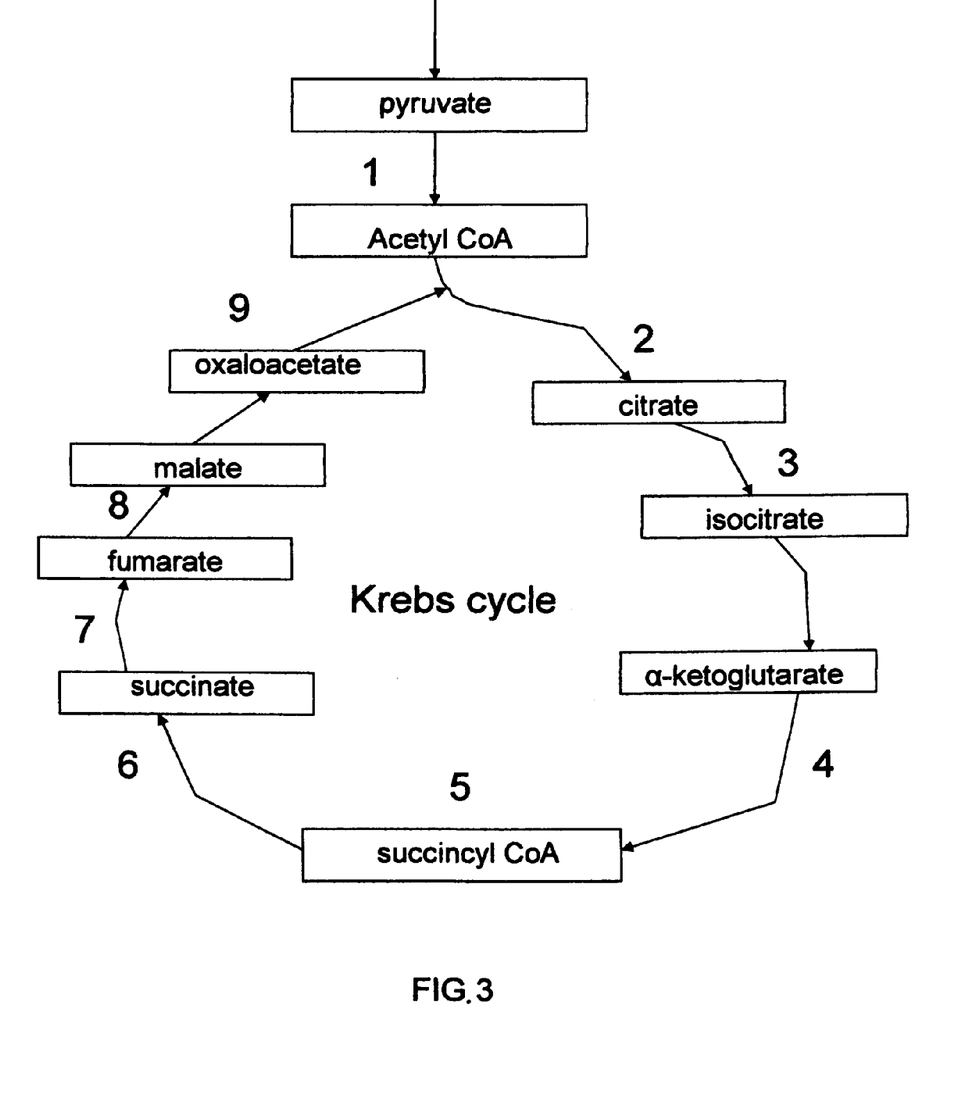
FIG. 3 is the Krebs cycle which is the heart of the respiration cycle in the body.

As a comparison to the present invention, the human body's Krebs cycle in FIG. 3 also transports electrons to the mitochondria in a natural, microscopic version of the therapeutic electric clothing process. The Krebs cycle processes pyruvate molecules produced in FIG. 4 to form adenosine triphosphate (ATP) and is the primary energy source for the human body. In order to understand the role of pyruvate, understanding of the Krebs cycle, a series of biochemical events in the conversion of sugars and fats (carbohydrates and lipids) into ATP, is essential. Pyruvate (pyruvic acid) is created when sugars are metabolized. If sufficient oxygen is available, pyruvic acid is broken down through the Krebs cycle. In an anaerobic state, pyruvic acid is broken down anaerobically creating lactic acid, which is often produced in muscle tissue, along with free radicals, during over-exertion, causing pain and fatigue.

Figure 4:
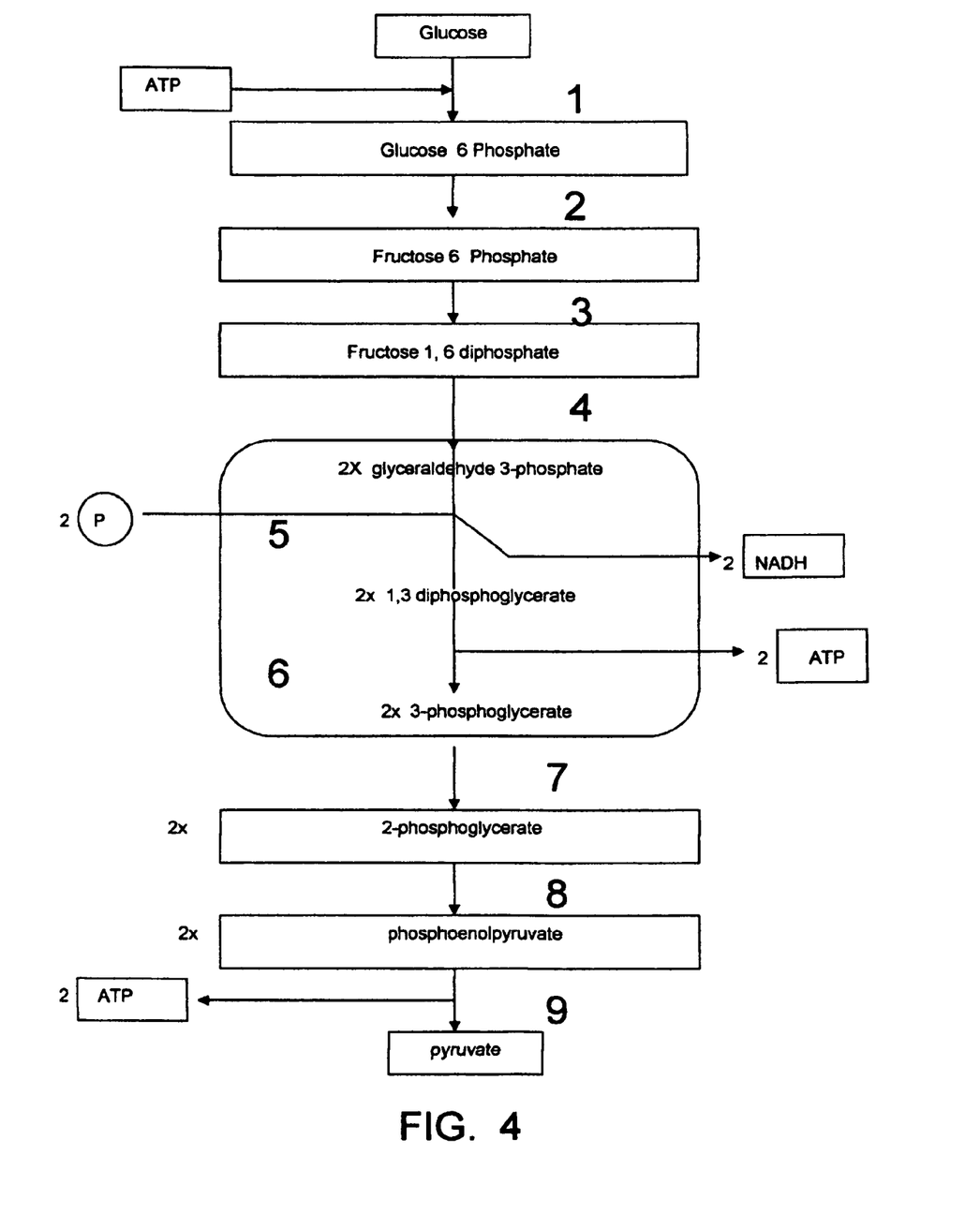
FIG. 4 is the glycolosis cycle which metabolizes sugar in the body.
Figure 5:
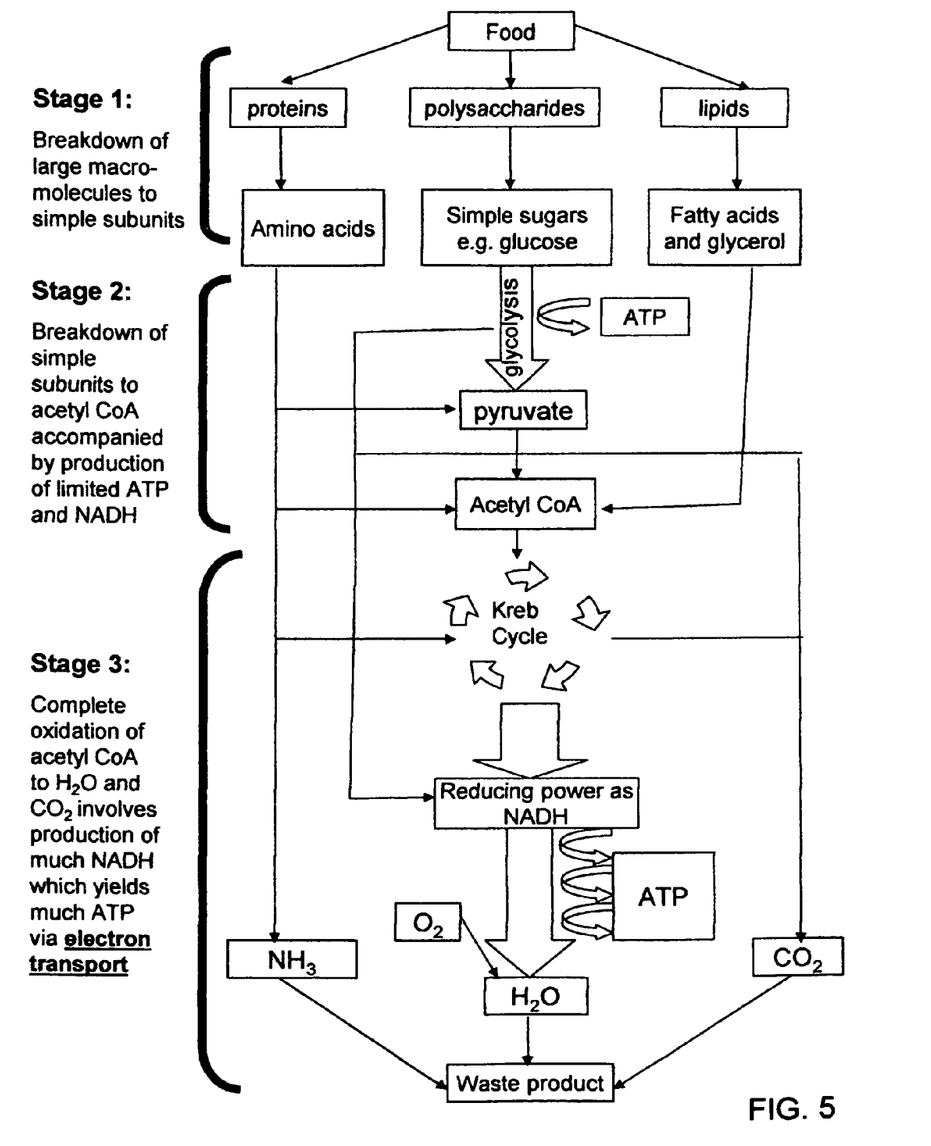
FIG. 5 is the complete respiration cycle in the human body containing the glycolosis cycle and Krebs cycle in the center with electron transport.

The process of converting glucose through glycolosis in FIG. 4 is necessary in order to produce the pyruvate molecules for the Krebs cycle. The important part of this energy conversion process in the body is shown in the complete respiration cycle in FIG. 5. The molecules which have been reduced in the Krebs cycle, in the center of the diagram, receive high energy electrons from the pyruvate molecules and represent energy to do work. Carrier molecules, much like hemoglobin in the blood, transport the high energy electrons and hydrogen protons to the inner mitochondrial membrane of the human body. Transferring energy during the transport, the electrons finally participate in the combining of $H_2$ and oxygen to form water. This is referred to as the "electron transport chain" in biology which demonstrates the vital role that electrons play in the energy metabolism of the human body.

Figure 6:
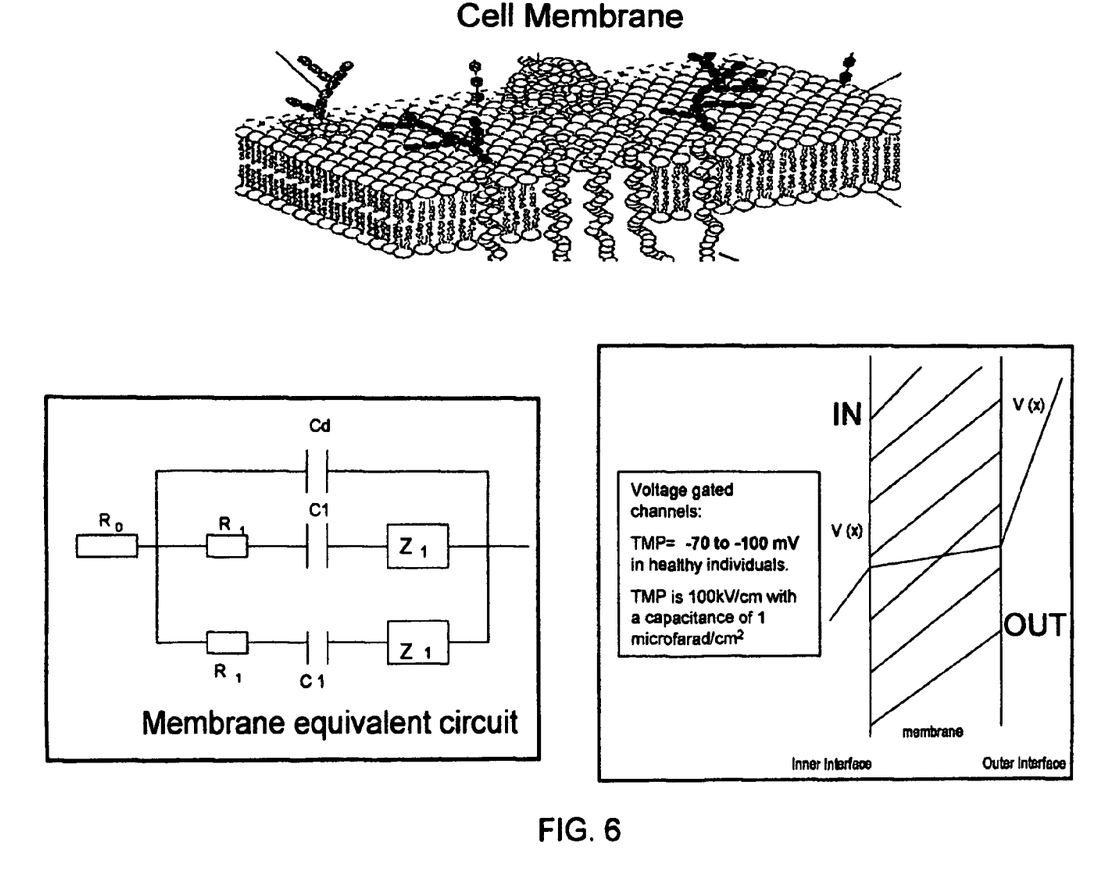
FIG. 6 is a composite image showing the important components of the human cell membrane.

FIG. 6 shows the composite image of the important components of the human cell membrane which forms a capacitor for storing electrical charge through ion transport across the cell membrane. This is the primary mechanism of transfer of electrical ions, which include electrons that may also form negatively charged ions from the present invention, into deeper cell layers as well as the intercellular fluid medium, bloodstream and lymph system of the biological terrain. FIG. 6 is an aid to the understanding of the human cell membrane, along with the electric field levels from inside the cell (inner interface) through the membrane to the outer interface. This electric field is formed primarily from the transport of calcium and potassium ions across the cell membrane through energy-activated channels. It is also the basic component (including a dielectric) for the equivalent circuit only recently developed for the human body (Polk, C., & E. Postow, *Handbook of Biological Effects of Electromagnetic Fields*, CRC Press, 1986, p. 58). This unique property of the human body indicates an inherent adaptation and perhaps innate compatibility toward the presence of high voltage electric fields, probably due to the high transmembrane potential (TMP) gradient in healthy individuals, present across cellular membrane tissue. This surprisingly intense electric field, which averages 100 kV/cm or equivalently 10 MV/m as noted in our first figure, is extraordinary because it demonstrates the body's ability to withstand high electric field energy without dielectric breakdown. It is also known in biophysics to be one of the only two ways that the human body stores energy (electrical gradients or chemical gradients). The inventor has discovered that debilitated people, with or without accompanying disease, will respond to a five minute exposure of a high voltage therapy device and report an increase in their liveliness and vitality almost immediately. Therefore, the insight toward developing a longer term, lower dosage electric antioxidant device was born.

Figure 7:
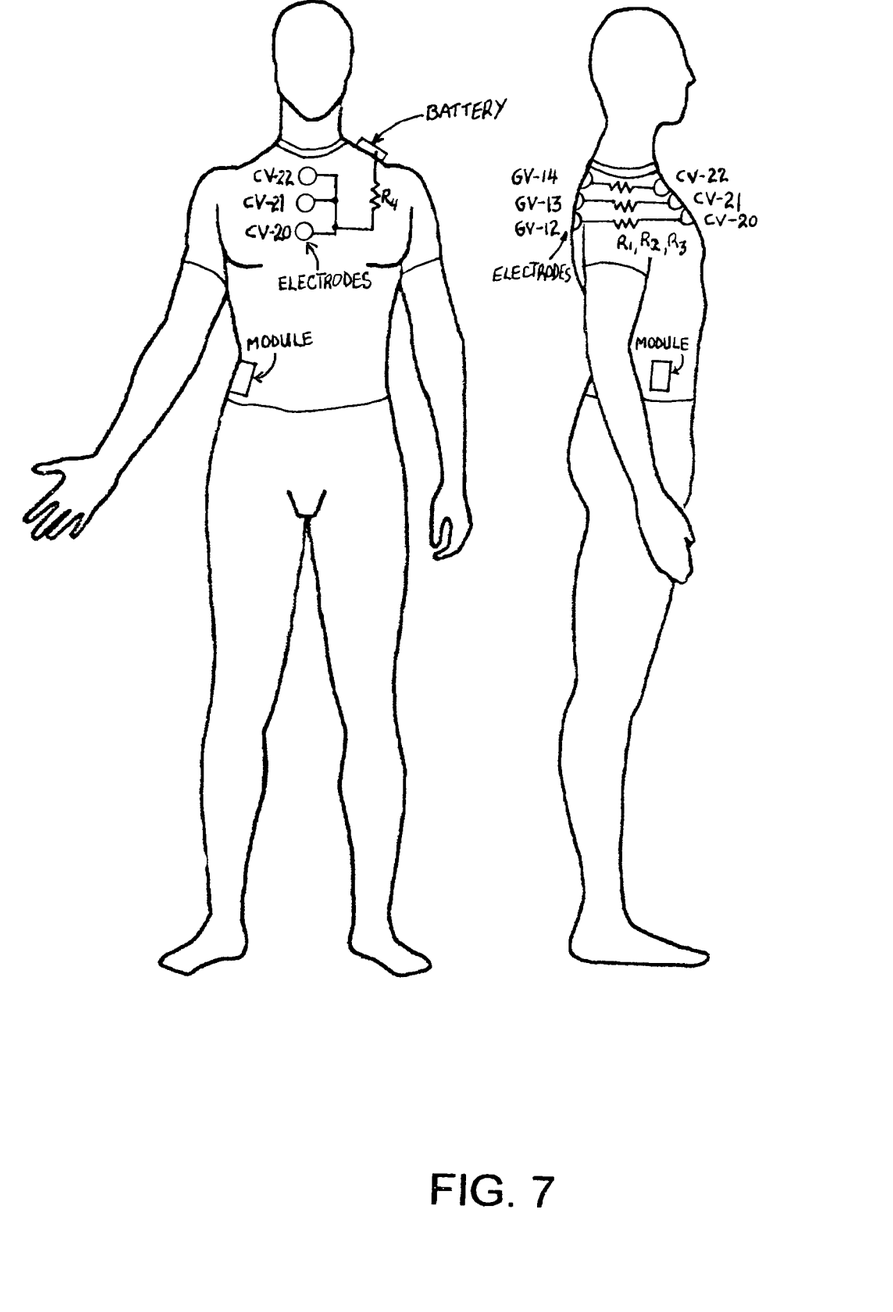
FIG. 7 is a schematic circuit diagram of the basic therapeutic electric clothing.

FIG. 7 shows the simplified circuit wiring diagram of the present invention with multiple skin resistances $R_1$-$R_3$ for parallel paths of multiple electrodes with a current-limiting resistor $R_4$ also added in series with the "battery" power source for safety purposes. The Module is an optional integrated circuit for specialized circuit response under various conditions in advanced designs. The $R_1$-$R_2$-$R_3$ parallel paths can possibly be the Governing Vessel (Du Mai) meridian acupuncture points GV-12, GV-13, GV-14 on the subject's back, added to the internal resistance of the body, communicating electrically and energetically to the Conception Vessel (Ren Mai) meridian acupuncture points CV-20, CV-21, CV-22 on the subject's front side, as one example of a preferred embodiment. The multiple contact electrodes are constructed preferably from silver-impregnated nylon, sold on the market under the trade name SilverIon® but can be made from any non-adhesive, non-oxidizing, electrical conductor, including conductive plastic or conductive fibers woven into a small patch to cover a particular point or set of acupuncture points. The electrodes are strategically located and imbedded or woven within the clothing to be exposed on the inside (skinside) to access and stimulate with electroacupuncture as well as to induce electric antioxidants through those access points known to be particular acupuncture points of interest for energy and vitality. Acupuncture points are chosen since they are points on the skin of lowered resistance and relatively high conductivity, among other reasons. It is preferred that the electric antioxidant clothing product does not have an on/off switch since the product can be removed when it is desired to turn it off and the clothing electron flow will reduce to a minimum or stop completely without the skin's low resistance pathway (measured to be in the range of 10 to 100 KΩ) being present. Since the human body assumes the electrical ground potential, which can be enhanced or stabilized by electrically conductive soled shoes, the flow of electrons out of one of the acupuncture electrodes is radial and equipotential from the electrode outward.

Figure 8:
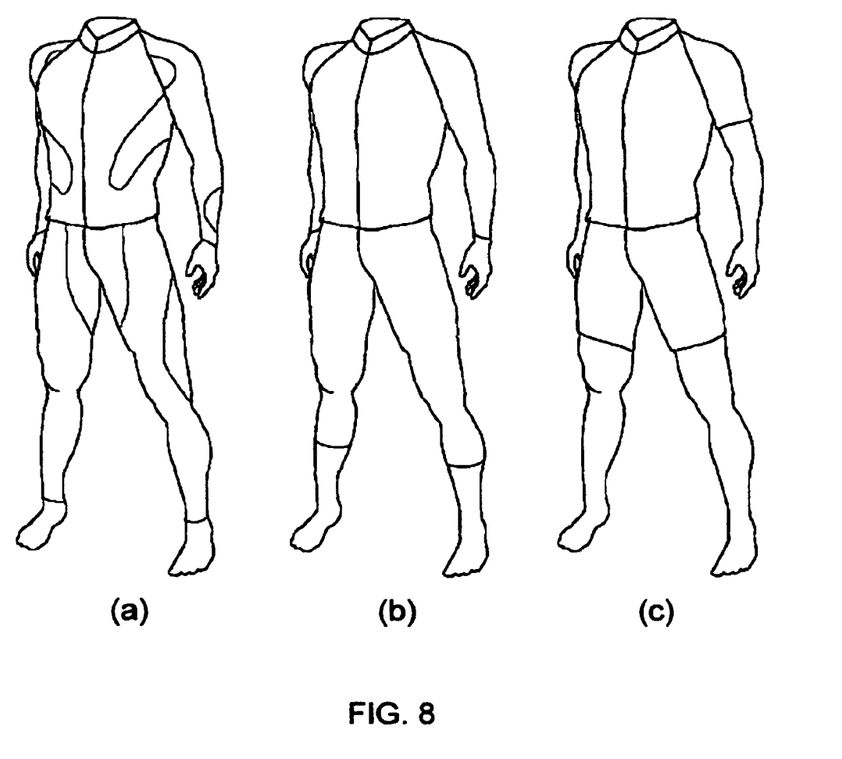
FIG. 8 is a selection of the (a) winter, (b) spring and fall, and (c) summer embodiments of the electric clothes body suit.
Figure 9:
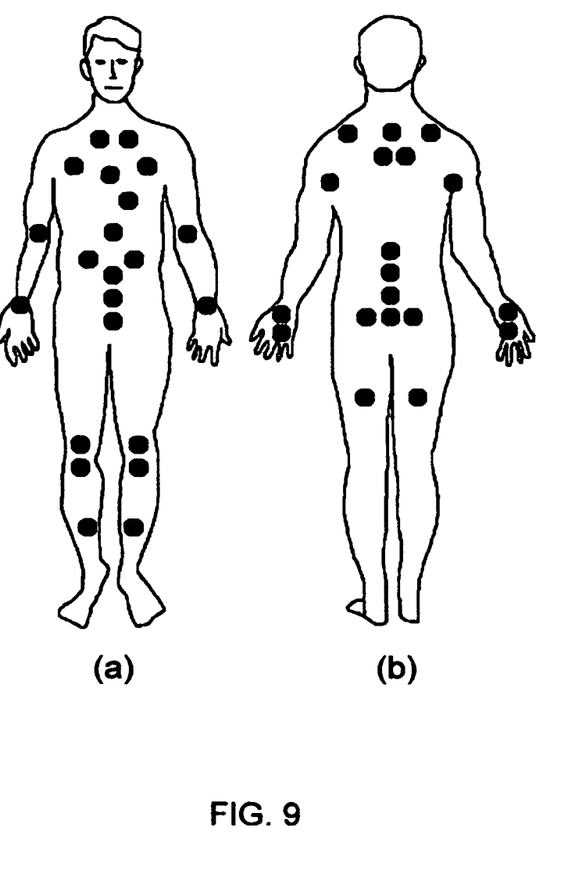
FIG. 9 is a diagram of the main acupuncture points on the (a) front and (b) back of the human body.

FIG. 8 shows a drawing of a test model of the electric therapeutic clothing suit with multiple, parallel wires imbedded vertically (not shown) in the full body suit model and a power-circuit Module on the belt (not shown). The professional Sports Model version of the electric therapeutic clothing is designed for (a) winter wear, (b) spring and fall use, and (c) summer wear. It contains one of several options for energy harvesting power sources such as thermoelectric devices imbedded in the clothing, or small flexible plastic solar cells that are sensitive in the infrared (IR) band as well as the visible light wavelengths, along with an integrated circuit electronic Module and optional wireless controller.

The hot weather short bodysuit design (FIG. 8c) of the electric therapeutic clothing is entitled, the Sports Model. It is designed to be retrofitted to ergonomic sports clothing products such as the Neosport Lycra or Neoprene bodysuits, for example. Extensive wiring and multiple electrode contacts and switching pathways, controlled by the IC electronic Module, can be integrated into a bodysuit for superior performance, under varying conditions. The Sports Model may also take advantage of an optional wireless controller, attached to the wrist, arm, or the waist, which can be designed to be programmed with a time-sensitive control of the electric antioxidant dosage as well as a level-sensitive dosage for mild, medium, or strenuous workouts for example. The Sports Model, in its preferred embodiment of the present invention is designed to be tailored to the athlete's needs and preferences, in order to be versatile and flexible. In this way, the marriage of the electric antioxidant-generating bodysuit with complete programmable control and the free radical-generating athlete can be tuned to perfection. It is possible that an advanced version of the Sports Model may include an LED style bargraph to indicate the instantaneous levels of electric antioxidant dosage (current level) and possibly a second LED style bargraph of a different color to show some biofeedback sensor parameter that is correlated to the body's production of free radicals. In this way, the beauty of the invention can be fully realized with a definitive method for the athlete to know when to increase or decrease the dosage or simply choose another program for the mild, medium, or strenuous levels available.

Another choice of programming for the Sports Model is to switch from constant-current circuitry to a constant-voltage circuitry, with appropriate user-friendly names such as Steady Going and Big Push, respectively. The constant voltage (Big Push) setting of the circuit may be preferred in a strenuous setting of workout, such as a competition, so that the electric antioxidant current may be allowed to increase when the skin resistance drops as the exertion level increases, thus synergistically delivering the much-needed antioxidant protection at the levels instantaneously required. The Big Push setting is also compatible with low, medium, and high options of constant voltage as well, for three further range options under that setting. The constant current (Steady Going) setting of the circuit is an alternative design for the non-competition mode which delivers a steady current that does not vary. The Steady Going setting is also compatible with the low, medium, and high options of constant current delivery as well, for three further options under that setting.

FIG. 10 shows an artist rendering of the main acupuncture points that can be accessed by electrodes on (a) the front human skin of the wearer and (b) the back side of the human body. A trained professional acupuncturist will understand the benefits derived from electroacupuncture and therefore, the present invention comprising electric microcurrent stimulation of one or more of these acupuncture points.

Product Benefits

There are many benefits to electronic or electric therapy. It is known to help speed the healing process, reduce swelling and inflammation, treat acute and chronic pain, release muscle trigger points, and improve soft tissue regeneration. Conditions which can be treated with electric clothing microcurrent therapy include the following, which represents only a few of the many conditions which can be treated. In addition, the following items represent broad categories for which there are many variations depending on the specific disease. The categories include structural maladies, auto-immune disorders, endocrine system imbalances, electromagnetism sensitivities and overexposures, muscle balancing, spine and brain disorders, body chemistry, injuries to joints, tendons, tissues. The therapeutic electric clothing microcurrent can also assist in repairing free radical damage associated with immune system disorders, weakness, challenges, and diseases, as well as relieving pain and possibly extending telomere length in DNA. It is also suitable for use in neurological control and toxicological problems.

The main benefits and purpose for the therapeutic electric clothing is:
  To provide continuous, healthy antioxidant protection to the human body.
  To provide increased percutaneous and transcutaneous current flow across the skin surface during exercise or exertion.
  To help prevent disease, debilitation, decrease in immune system performance all of which contribute to the aging process.
  To aid the immune system in fighting free radicals by providing antioxidant electrons to the skin.
  To enhancing body performance and endurance related to energy and vitality.
  To aid and help treat conditions and diseases and improve health and wellness, as well as improve lifespan and longevity.

Preferred Circuit Embodiment

The preferred embodiment of the therapeutic electric clothing is now delineated. The therapeutic electric clothing may comprise a T-shirt, tights, underwear, socks, hats, skullcaps, gloves, shoes, or ski masks. Such clothing will include conductive electrodes woven into the clothing to maintain contact with the skin and insulated conductive fibers also woven into the clothing to carry a direct current (DC), pulsed DC current, or an alternating current (AC) from a self-powered power source, with conductive electrodes such as SilverIon® for disinfecting, sports injury accelerated healing and anomalous deep tissue therapeutic benefits, as reported by its inventor, Bart Flick, M.D, at the Whole Person Healing Conference in Washington D.C. in 2004. A potential miniature power source is the Quallion QL00031 rechargeable lithium ion cell 12 mm in length and is biocompatible and light weight. However, the preferred power source that fulfills the concept of a self-powered power source without need for recharging is the Nextreme UPF40 thermoelectric converter that is only a few millimeters in size and generates sufficient current from body heat. Another example is Konarka plastic solar cells which are sensitive in the infrared band that the human body emits. An electronic controller is an optional item for amplitude adjustment and time programming in an alternate embodiment.

Options for the conductive fiber circuit design include: transcutaneous electrodes, power source and wiring; percutaneous electrodes, power source and wiring; and subcutaneously implanted electrodes for wireless electrical transfer, power source and biocompatible wiring under the skin that obviates the need for clothing support by utilizing a modern bioelectrolyte fuel cell power source.

Advanced models for the therapeutic electric clothing may include a remote controller that is wireless and an LED indicator light and/or bargraphs on the clothing.

Electric Therapeutic Clothing Embodiments

The therapeutic electric antioxidant clothing preferably is made of skin tight stretchable fabric to maintain conductive contact with the skin in the strategic acupuncture locations. For the sports model embodiment, full body suit electric therapeutic clothing including built-in socks or separate electric therapeutic clothing socks is preferred so that the acupuncture points of the feet can also be selectively activated. A Sports Model, even without foot covering such as shown in FIG. 8, is also capable to be designed to increase the microcurrent amperage during increased exertion since the skin becomes more electrically conductive when the body perspires. A special embodiment elastic band or stretchable skullcap for the head is a suitable application for the invention, as well as an integrated therapeutic electric clothing wristband, armband, or legband of elastic or stretchable material.

The Sports Model therefore is preferably designed to be synergistic to the needs of an athlete, quenching the increased free radicals during exertion with proportionally increased microcurrent. It is anticipated that such a novel therapeutic sports model electric clothing for athletes will undoubtedly increase performance and endurance levels beyond the personal best that the athlete has previously attained. This is a predictable benefit since free radical production is well known to increase with exertion which contributes to sports fatigue.

The above descriptions and illustrations are only by way of example and are not to be taken as limiting the invention in any manner. One skilled in the art can substitute known equivalents for the structures and means described. The full scope and definition of the invention, therefore, is set forth in the claims.

What is claimed is:

1. A method for applying therapeutic electric antioxidant microcurrent through clothing to human skin of a living person comprising the steps of:
    interweaving conductive fiber wiring into clothing which may include conductive silver-impregnated nylon fibers woven into a small patch on a skinside of the clothing thus constructing one or more conductive electrodes;
    contacting the human skin with at least two of the conductive electrodes;
    locating an electronic power-circuit module between a self-contained microcurrent power source and the conductive electrodes, each imbedded in the clothing;
    connecting the conductive fiber wiring to the microcurrent power source, the electronic power-circuit module and to the conductive electrodes;
    and
    applying a direct, pulsed or alternating microcurrent to particular acupuncture points on the human skin through the conductive fiber wiring and the electronic power-circuit module connected to the conductive electrodes for the therapeutic purpose of conducting electric antioxidants to the human skin.

2. A process for introducing therapeutic dosage of electric antioxidants to living human skin where the process is integrated into clothing comprising:
    means for electrically contacting the skin which is integrated into clothing in the location of at least two acupuncture points;
    means for applying direct, pulsed or alternating microcurrent, integrated into clothing, connected to the means for electrically contacting the skin;
    means for interweaving conductive pathways of electricity into clothing the means which is in nonconductive contact with the skin while connected with the means for applying microcurrent and to the means for electrically contacting the skin; and
    means for electronically controlling the electric antioxidant therapeutic dosage introduced to the human skin while integrated into clothing and while connected to the means for applying microcurrent.

3. A process for introducing therapeutic dosage of electric antioxidants to the human skin according to claim 2, further comprising:
    means for wirelessly programming the means for electronically controlling the electric antioxidant therapeutic dosage introduced to the human skin.

4. The method of claim 1 where the microcurrent power source applies a pulsed direct current.

5. The method of claim 1 where the electronic power-circuit module is controlled by a wireless controller attached to the wrist, arm, or the waist, which can be programmed and is powered by an energy harvesting power source such as a thermoelectric device imbedded in the clothing.

6. The method of claim 1 where the interwoven clothing is a stretchable shirt and the microcurrent power source applies a pulsed direct current.

7. The method of claim 1 where the interwoven clothing is a bodysuit and the microcurrent power source applies an alternating current (AC) or a pulsed direct current.

8. The method of claim 1 where the interwoven clothing is a headband and the microcurrent power source applies a direct current (DC).

9. The method of claim 1 where the interwoven clothing is socks and the microcurrent power source applies a direct current (DC).

10. The process of claim 2 further comprising a means for showing a biofeedback sensor parameter.

11. The process of claim 3 where the means for wirelessly programming includes setting a constant-current microcurrent or a constant-voltage microcurrent in the means for electronically controlling the electric antioxidant therapeutic dosage introduced to the human skin.

12. The method of claim 1 where the step of contacting the human skin with at least two of the conductive electrodes includes positioning a first conductive electrode on the skinside of the clothing and strategically located near to one of the Conception Vessel (Ren Mai) meridian acupuncture points CV-20, CV-21, CV-22 on the subject's front side and a second conductive electrode on the skinside of the clothing and strategically located near to one of the Governing Vessel (Du Mai) meridian acupuncture points GV-12, GV-13, GV-14 on the subject's back.

13. An apparatus for generating therapeutic electric antioxidant microcurrent in clothing skinside to a living human person comprising:
    conductive silver-impregnated nylon fiber wiring interwoven in clothing which may include conductive silver-impregnated nylon fibers woven into a small patch on a skinside of the clothing;
    at least two or more conductive electrodes each consisting of the woven small patch in contact with the human skin;
    an electronic power-circuit module imbedded in clothing and located between a self-contained microcurrent power source imbedded in clothing and the conductive electrodes;
    additional electrically conductive fiber wiring connected between the electronic power-circuit module and the conductive electrodes and the microcurrent power source adapted for generating a direct, pulsed or alternating current to particular acupuncture points on the human skin through the conductive silver-impregnated nylon fiber wiring and the electronic power-circuit module connected to the conductive electrodes for the therapeutic purpose of conducting electric antioxidants transcutaneously into the human skin.

* * * * *